(12) United States Patent
Arnoldsen, Jr. et al.

(10) Patent No.: US 9,914,942 B2
(45) Date of Patent: Mar. 13, 2018

(54) COMPARTMENTALIZED ANAEROBIC DIGESTERS

(71) Applicants: Ronald E. Arnoldsen, Jr., Huntingdon, PA (US); Debra A. Arnoldsen, Huntingdon, PA (US)

(72) Inventors: Ronald E. Arnoldsen, Jr., Huntingdon, PA (US); Debra A. Arnoldsen, Huntingdon, PA (US)

(*) Notice: Subject to any disclaimer, the term of this patent is extended or adjusted under 35 U.S.C. 154(b) by 59 days.

(21) Appl. No.: 14/684,846

(22) Filed: Apr. 13, 2015

(65) Prior Publication Data
US 2015/0218591 A1 Aug. 6, 2015

Related U.S. Application Data

(63) Continuation-in-part of application No. 13/710,448, filed on Dec. 10, 2012, now Pat. No. 9,005,443.
(Continued)

(51) Int. Cl.
| C02F 3/28 | (2006.01) |
| C12P 5/02 | (2006.01) |
| C12M 1/107 | (2006.01) |
| C12M 1/12 | (2006.01) |
| C02F 11/04 | (2006.01) |
| C12M 1/00 | (2006.01) |
(Continued)

(52) U.S. Cl.
CPC .............. *C12P 5/023* (2013.01); *C02F 3/284* (2013.01); *C02F 11/04* (2013.01); *C12M 21/04* (2013.01); *C12M 23/04* (2013.01); *C12M 23/06* (2013.01); *C12M 23/34* (2013.01); *C12M 23/36* (2013.01); *C12M 33/00* (2013.01); *C12M 41/22* (2013.01); *C12M 43/00* (2013.01); *C12M 47/18* (2013.01); *C02F 2103/20* (2013.01); *Y02E 50/343* (2013.01); *Y02W 10/23* (2015.05); *Y02W 10/37* (2015.05)

(58) Field of Classification Search
CPC .... C12P 5/023; C02F 2201/007; C02F 11/04; C02F 3/28; C02F 3/284
USPC ................ 210/603, 179, 260, 613, 151, 218
See application file for complete search history.

(56) References Cited

U.S. PATENT DOCUMENTS

| 4,897,195 A | * | 1/1990 | Erickson ............. C05F 17/0081 210/170.05 |
| 6,673,243 B2 | | 1/2004 | Srinivasan et al. |
| (Continued) | | | |

FOREIGN PATENT DOCUMENTS

DE    10 2010 010 294 A1    9/2011

OTHER PUBLICATIONS

Schneider, English machine translation DE 102010010294, Sep. 2011, pp. 1-6.

*Primary Examiner* — Claire A Norris

(57) ABSTRACT

An anaerobic digestion device includes a digester body with an opening through which organic waste is received and a digester drum removably inserted into the digester body for receiving the organic waste. The digester drum is movable relative to the digester body to advance a slurry of the organic waste along a length of the digester body. A set of ports spaced along the digester body and arranged to vent biogas from the organic waste contained in the digester drum. A storage vessel is configured to receive and store biogas received from the digester body via the ports, and a heating system configured to heat the digester body. The heating system is fuelled by the biogas vented from the digester body.

1 Claim, 4 Drawing Sheets

Related U.S. Application Data

(60) Provisional application No. 61/568,173, filed on Dec. 8, 2011.

(51) Int. Cl.
    *C12M 1/26*     (2006.01)
    *C12M 1/02*     (2006.01)
    *C02F 103/20*     (2006.01)

(56) References Cited

U.S. PATENT DOCUMENTS

| | | | |
|---|---|---|---|
| 7,320,753 B2 * | 1/2008 | Roos | A01C 3/023 |
| | | | 210/603 |
| 7,563,371 B2 * | 7/2009 | McCune-Sanders | C12M 21/04 |
| | | | 210/603 |

* cited by examiner

COMPARTMENTALIZED ANAEROBIC DIGESTERS

RELATED APPLICATIONS

This application claims priority to U.S. Nonprovisional application Ser. No. 13/710,448, filed 10 Dec. 2012, which claims priority to U.S. Provisional Patent Application No. 61/568,173, filed on 8 Dec. 2011, the disclosures of each of which are incorporated herein by reference in their entireties.

BACKGROUND

1. Technical Field

The present disclosure relates to anaerobic digesters and more specifically to compartmentalized anaerobic digesters.

2. Introduction

Conventional anaerobic digesters include plug-flow digesters, lagoon-type digesters, and batch digesters. A conventional plug-flow digester is described in U.S. Pat. No. 6,673,243 to Srinivasan et al., the disclosure of which is incorporated herein by reference. This plug flow digester includes a reactor divided into a number of connected chambers that retain fluid and manure/compost slurry. The digester of the '243 patent utilizes a continuous fermentation in a single, large batch size. The flow of waste (i.e., the chamber segments each containing manure/organic waste slurry) is directed through the digester to ensure that the waste passes through each chamber before exiting the digester.

The single, large batch size of the '243 patent is disadvantageous because the slurry can sit still for lengths of time, flow passages can become clogged, production of biogas can take longer, and the operator has no control over the temperature of the digestor or the amount of time that the slurry remains in each chamber segment. Thus the system of the '243 patent can be unpredictable.

Some conventional digesters also include moving parts (e.g., and auger or other mixing device) that must be powered. Such a design thus uses more energy to create the biogas, resulting in a less energy-efficient system. The moving parts can also lead to undesirable breakdowns and associated repair time and expenses. Also, some conventional digesters do not operate well in cold temperatures.

Therefore it may be desirable to provide an inexpensive and easy-to-build compartmentalized anaerobic digester that gives an operator more control of the digestate through temperature and pH adjustment. Such control may be achieved by adjusting speed of movement of the slurry/digestate through the digestor, thereby varying the length of digestion time.

SUMMARY

According to various aspects of the disclosure, an anaerobic digestion device includes a digester body configured to receive organic waste and a set of plates coupled to one another so as to divide an interior volume of the digester body into a set of compartmentalized chambers. The compartmentalized chambers are movable relative to the digester body to advance a slurry of the organic waste along a length of the digester body. A set of ports can be spaced along the digester body and arranged to vent biogas from the digester body.

In some aspects of the disclosure, a method for anaerobic digestion of organic waste includes receiving organic waste into one of a set of compartmentalized chambers of a digester body, moving the compartmentalized chambers relative to the digestor body during the digestion process, collecting biogas from the chamber at various ports spaced along a length of the digester body, and outputting a digestate from the digester body.

According to various aspects of the disclosure, an anaerobic digestion device includes a digester body configured to receive organic waste and a set of plates coupled to one another so as to divide an interior volume of the digester body into a set of compartmentalized chambers. The compartmentalized chambers are movable relative to the digester body to advance a slurry of the organic waste along a length of the digester body. A set of ports spaced along the digester body and arranged to vent biogas from the digester body. A storage vessel is configured to receive and store biogas received from the digester body via the ports, and a heating system configured to heat the digester body. The heating system is fuelled by the biogas vented from the digester body.

In addition, digester drums can be incorporated into the design to ensure that new organic waste is never mixed with old organic waste. One such result of using digester drums in this manner is that pathogens from new organic waste are never introduced into partially or completely processed organic waste. The digester drums are arranged within a pipe or tube, so that collecting the organic waste is tidier and more confined. Digester drum inserts can enhance containment, and reinforce other mechanisms for preventing the mixing of different 'batches' of organic waste.

Digester drums can be a modification of the general plate separation design disclosed herein. Digester drums can be inserted to further separate batches so that independent water content, temperature, pH balance, and/or other variables can be manipulated at different stages of the digestion process. In this way, the variable affecting the organic waste in one digester drum can be controlled individually and separately from other digester drums.

In one example experimental embodiment, the digester drums were modified 55-gallon drums used in addition to the separator plates for neater containment and supportive materials for hoist movement of the chambered sections. However, in one alternative arrangement, the plates can be eliminated or removed without any change in the biological system itself. Therefore, larger drums, such as a 130-gallon drum, can be incorporated instead. In one variation, a barge made of plastic, wood, fiberglass, or other material, such as a longitudinal half of a 55-gallon drum (or any other size plastic drum), can be placed under the larger drums as a sled or carriage. Then, when the drums need to be moved, the barge can be used as a pulling device for the drums. This approach allows for the drums to be moved while avoiding damage to the drums themselves. The barges may be made of material that is relatively inexpensive compared to the drums. Then, in the case the barges are damaged, the replacement cost is reduced. Various pull chains or other manipulation mechanisms, linkages, or handles are then attached to the barge, and do not penetrate the anaerobic digestion chambers. The pull chains, manipulation mechanisms, linkages, or handles can be optionally removably coupled to the barge for replacement or for reuse with other barges. The barge can include multiple attachment receptacles, connectors, or housings for one or more different types of chains, linkages, and so forth.

Further advantages and embodiments may be apparent from the appended drawings.

DETAILED DESCRIPTION

Figure 1:
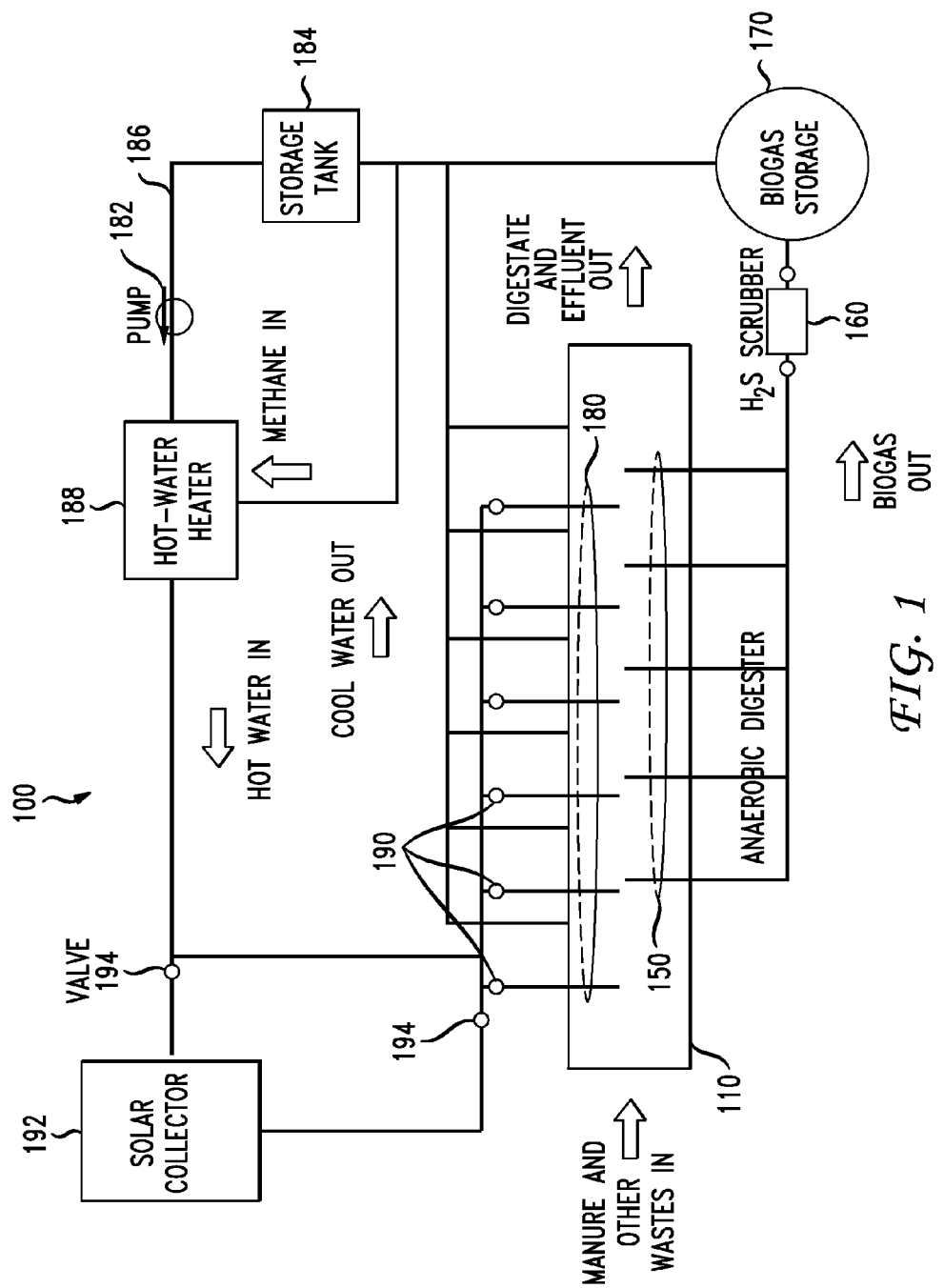
FIG. 1 shows a schematic representation of an exemplary anaerobic digestion system in accordance with various aspects of the disclosure.

FIG. 1 shows a rough schematic representation of an exemplary anaerobic digestion system 100 in accordance with various aspects of the disclosure. As shown in FIG. 1, manure and/or other organic waste (e.g., vegetables and vegetable plant parts from produce production, unused hay from livestock feed, or grass clippings) is fed into an anaerobic digester body 110. During retention time of waste in the digester body 110, biogas (i.e., a gaseous mix of primarily methane and carbon dioxide) is generated from methanogenic microorganisms and collected from the top of the digester 110 via one or more ports 150. The collected biogas is fed along piping through a hydrogen sulfide scrubber 160 and ultimately to an expandable storage vessel 170, such as for example, a biogas bag.

In order to keep the digester body 110 warm during colder weather, hot water may be pumped through tubing/piping 180 outside of the digester body 110. The water cycle includes a pump 182 configured to pump water or a water/anti-freeze mixture from a storage tank 184 through flow lines 186 to a water heater 188 and further to the tubing/piping 180 wound about the circumference of the digestor body 110 and back to the storage tank 184. To heat the water, after biogas production has begun, biogas extracted from the digester body 110 can be used to fuel the hot water heater 188. Valves 190 may be placed strategically along the length of the digester body 110 to help facilitate control of the heating of the digester body 110. In some aspects, supplemental heat may be supplied to the hot water heater 188 by means of a solar collector 192 to help initiate warming until biogas production commences or when additional heat is needed. In some aspects, solar radiation absorbed through the collector will be used to initialize the process. The solar collector may be turned off or on through one or more valves 194 which help prevent temperature loss during night.

Figure 2:
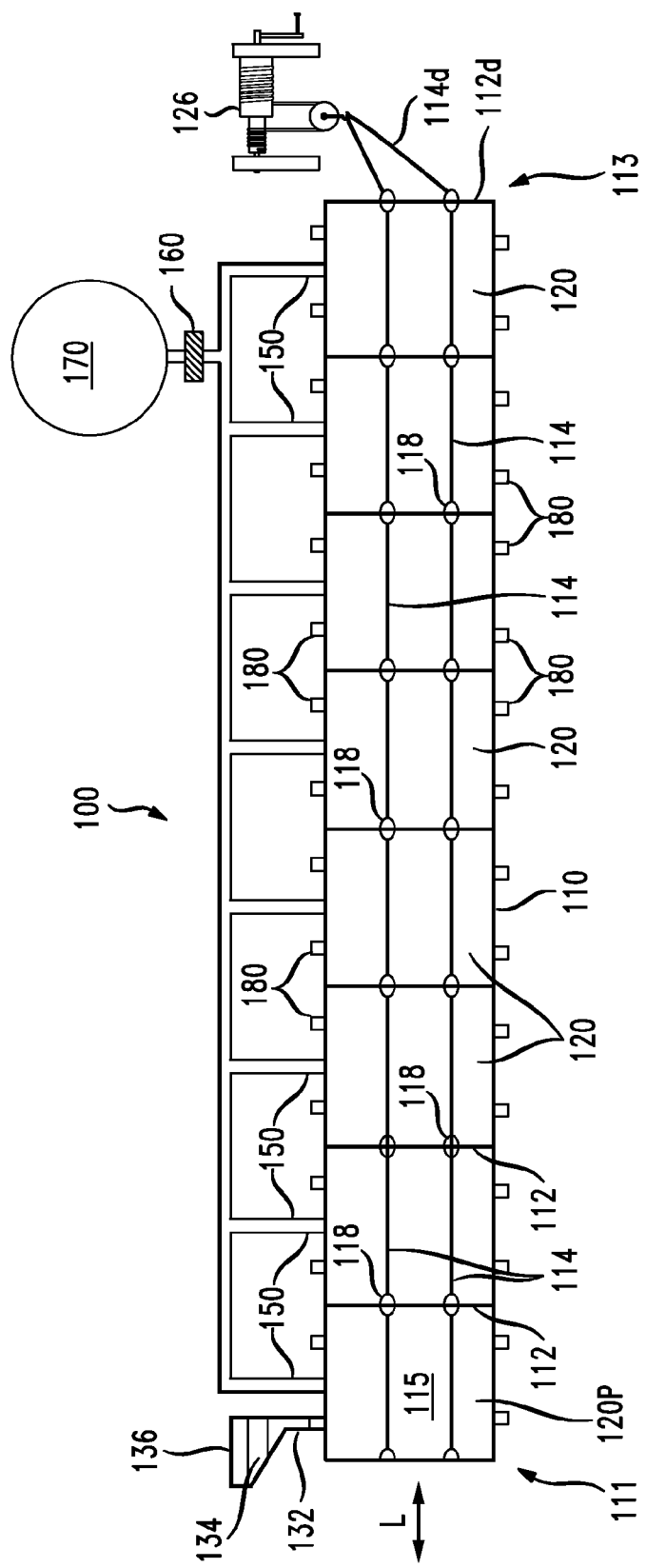
FIG. 2 shows a diagrammatic cross-sectional view of elements of the anaerobic digestion system of FIG. 1.

Referring now to FIG. 2, according to various aspects, the digester body 110 of the anaerobic digestion system 100 may be made up a cylindrical vessel, such as for example, a high density polyethylene corrugated storm drain pipe, having a proximal end 111 and a distal end 113. In some exemplary aspects, the digester body 110 may be made of a large corrugated polyvinyl butyl storm water pipe with a rough interior dimension of 3 feet, for example.

The volume of the digester body 110 is compartmentalized by scraper plates 112. For example, in some exemplary embodiments, the digester body 110 may have a length of 32 feet, which is compartmentalized into eight chambers 120 by nine scraper plates 112 sequentially spaced about four feet apart from each adjacent plate. The scraper plates 112 may be shaped and sized to match the interior transverse cross-sectional shape and dimension of the digester body 110 so that slurry cannot flow between compartments. For example, following the example of the preceding paragraph, the plates 112 may be circular shaped with an approximately 3-foot diameter. The plates 112 may be constructed of a metal (e.g., steel), a polymer (e.g., HDPE or polypropylene), or any inert material. Rubber seals (not shown), for example, inflated with air, about the circumference of the plates may be used in conjunction with the plates 112 to minimize any mixing of fluids between compartments. Alternatively, seals may be constructed of polyethylene, foam, or the like.

In the present digestion system 100, the compartmentalized chambers 120 are moved along the longitudinal direction L relative to the digester body 110. This movement is facilitated by the seals about the periphery of the plates 112.

It would be understood by persons skilled in the art that the plates 112 may be dimensioned slightly smaller than the interior cross-section of the digester body 110 so as to allow sliding movement of the plates 112 in the longitudinal direction relative to the digester body 112. Plates 112 may be designed with a thickness selected to avoid tipping of the plates 112 within the digester body 110. For example, in some aspects, the plates may have a thickness of 3"-10", for example, about 8". It should be appreciated that the length of the digester body, the length of the compartmentalized chambers, and the number of chambers can be varied according to the desire of the operator.

Figure 3:
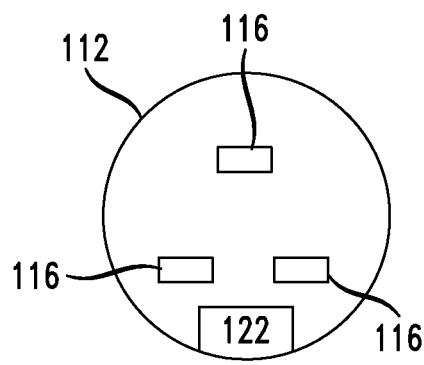
FIG. 3 shows a diagrammatic front view of an exemplary scraper plate in accordance with various aspects of the disclosure.
Figure 4:
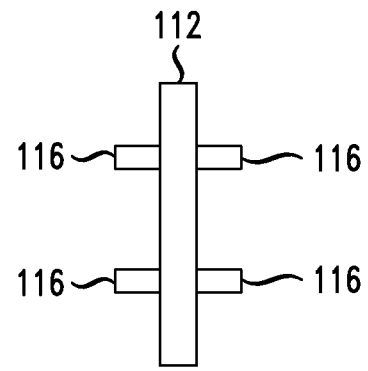
FIG. 4 shows a diagrammatic side view of the scraper plate of FIG. 3.

In order to effectuate movement of the chambers 120 relative to the digester body 110, the scraper plates 112 are detachably coupled to one another via more pull members 114, for example chains or cables that extend through the digester body 110 in the longitudinal direction L. In some aspects, the system 100 may include a set of three chains or cables 114 extending substantially parallel to one another between each adjacent pair of scraper plates 112 in the longitudinal direction of the digester body 110. For example, following the example above of eight 4-foot compartmentalized chambers 120, the pull members 114 may be about 4 feet in length. Each scraper plate 112 may have three connection members 116 attached to each of its flat surfaces (i.e., sides), as illustrated in FIGS. 3 and 4. Each pull member 114 may have a connector 118 at each of its ends. The connector 118 and connection members 116 cooperate to removably couple the pull members 114 to the scraper plates 112.

In some aspects, the connection members 116 may be made up U-bolts welded to each side of each plate, effectively allowing a chain to be removably fixed thereto and allowing the plates 112 to be moved in the longitudinal direction relative to the digester body 110. To minimize twisting and turning of the plates 112, an equalizing member 122 could be affixed (e.g., welded) to the bottom of each plate 112, which may allow the weight of the fluid and biomass inside the digester body to keep the plate 112 plumb as it translates along the longitudinal dimension of the digester body. It should be appreciated that more than three or less than three pull members 114 may be used between adjacent scraper plates. The one or more pull members 114d extending distally from the distal-most scraper 112d would then be coupled to a winch system 126 that pulls the plates through the digester body 110. The size/strength of the pull members 114, including distal pull members 114d, can be selected based on the expected load of the entirety of all scraper plates 112 and slurry. In some aspects, the distal pull members 114d may vary from the other pull members 114. The winch system 126 can be operated manually or automatically.

It should be appreciated that other designs for the scraper plates and pull members could be utilized. For example, each scraper plate may have a notch cut into the plate to allow a chain to pass through and removably interlock. This design would allow the scraper to move throughout the digester body, but may allow contamination between compartments to occur and/or may allow the introduction of oxygen to an otherwise anaerobic environment (i.e., everything under water).

Figure 5:
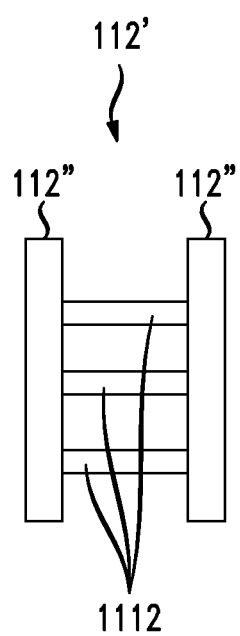
FIG. 5 shows a diagrammatic side view of an exemplary scraper plate arrangement in accordance with various aspects of the disclosure.

Referring to FIG. 5, a single scraper plate may be replaced by a scraper plate arrangement 112'. For example, the scraper plate arrangement 112' may include two or more plate members 112" coupled together, for example, via one or more spreader bars 1112. Three spreader bars 1112 are shown coupling the two plate members 112" in FIG. 5. In some aspects, the plate members 112" may be spaced apart a desired distance selected to avoid tipping of the plate members 112" within the digester body 110. For example, in some aspects, the plate members may be coupled by 3"-10" spreader bars 1112, for example, about 8" spreader bars 1112. It should be appreciated that each plate member may include an individual peripheral seal, as described above, or the plate arrangement 112' may include a single peripheral seal.

The digestion system may include an inlet 130 at the proximal end 111 of the digester body 110. The inlet 130 opens to the interior volume 115 of the proximal-most compartmentalized chamber 120p of the digester body 110. According to some aspects, the inlet 130 may contain a stand pipe 132 in which a spring-loaded input valve 134 catches the descending manure from an open grate 136, hence potentially minimizing odors from escaping. Upon appropriate amounts of manure, the input valve 134 would open due to the weight of the manure and release the manure down into the volume 115 of the proximal chamber 120p of the anaerobic digester body 110. After releasing the manure and/or fluid, the input valve 134 would then spring back into to its original position and provide a quality seal in which no offensive odors would be able to escape. Thus, the input valve 134 allows manure and/or other organic waste to enter the inlet of the anaerobic digester and prevent offensive odors from escaping into the surrounding environment. Since pigs are trainable as to where to relieve their manure, the input valve 134 may be termed a "pig toilet." Alternatively or additionally, the inlet may be manually opened and/or closed or may include an open system in which manure passively enters the digester through an open grate. However, such a design may permit odors to arise from the digester inlet and into the environment.

The anaerobic digestion system 100 includes one or more storage units 170 arranged to capture biogas produced from the anaerobic digester and vented from the digester body 110 via the one or more ports 150 on top of the body 110. Following the preceding example of eight compartmentalized chambers 120, the digestion system 100 may include eight ports 150—one corresponding with each chamber 120. For example, in the event of eight 4-foot chambers, a proximal-most port can be disposed about two feet from the proximal end 111 of the digester body 110 and then spaced every four feet on center along the longitudinal direction.

In some aspects, one or more of the ports 150 can be valved to monitor pressure, thereby assisting with the monitoring of the production of biogas. Each port may also be equipped with a sample collector (not shown) which can be used to manually test samples of corresponding chambers. Additionally or alternatively, each port, and thus each corresponding chamber, can be equipped with sensors to enable computerized monitoring of the system. The plates 112 and compartmentalized chambers 120 can be moved based on data retrieved from the ports 150.

The biogas can be stored until it is burned as a fuel source in the hot water boiler 188 or sent directly to the hot water burner 188 without storage. In some aspects, the system 100 may include one or more large storage units 170 constructed from high density polyethylene or polyvinyl chloride sheeting sealed into a bag and housed in a protective rigid 4-foot diameter pipe so that the bag could still expand. It should be appreciated that the biogas can also be stored and eventually sold commercially.

The anaerobic digestion system 100 may further include a heating system to keep the anaerobic digester in optimal operating conditions. In some exemplary aspects, water containing an anti-freezing solvent may be heated by the water heater 188 and then circulated through one or more flow lines 186, 180, for example, flexible hot water tubing (such as, e.g., PEX) or pipes, that encircle the circumference of the digester body 110. An insulator (not shown) may be placed about the hot water tubing and digester body 110 for efficiency.

In the example of a digester body being made of a corrugated pipe, the hose or pipe may lie in the hollow ribs of the corrugated pipe. In some aspects, the heated fluid may circulate from an inlet port and exit through an outlet port near the bottom of a rib. In some aspects, flow lines would be run through the ribs at greater frequency or in a doubled up format in areas where more heat is desired for greater biogas production (for example, more heating pipes initially for pre-warming of manure slurry and/or expediting methane production). In addition, numerous valves are placed strategically along the length of the digester's heating coil system allowing the digester operator the ability to select which sections to circulate more or less water/antifreeze fluid through the system. The manually or automatically controllable valves thus provide additional control to the temperature regulation of the digester.

The digestion system 100 may include a hydrogen sulfide scrubber 160 configured to remove offensive odors emanating from the hydrogen sulfide produced by the anaerobic digestion process. In some aspects, the biogas is passed through a column of iron filings, which removes the odors, as the biogas flows from the ports 150 to the storage vessel 170. The column of iron filings acts as a packed medium filter, which is already in use by digesters in European countries. In some aspects, oxygen from the oxidation of the biogas near the collection pipe of the biogas may be introduced. The oxygen precipitates the sulfur out of the hydrogen sulfide, and the sulfur precipitate falls into the effluent providing additional nutrition to the compost. In such a design, a pressure gradient would need to be maintained so that oxygen flows in rather than having biogas flow out.

In some aspects, the system 100 may include a pressure relief valve (not shown) after the hydrogen sulfide scrubber 160. The relief valve is controlled by hydrostatic pressure; that is, if the pressure exceeds the hydrostatic pressure, biogas will be discharged through the system through this valve. In addition a valve can be installed so that biogas can be burned off or as they say "flared" if excess gas is created that can't be stored. This may be facilitated by a pipe that comes off of the bag and goes to a pilot light where it is burned off preventing biogas from getting into the environment.

In operation, a first scraper plate 112, which becomes a distal-most plate 112*d* is coupled to the winch system 126 by distal pull members 114*d*. The winch system 126 moves the plate 112*d* distally a length approximate to the length of a chamber 120. Pull members 114 are then coupled to the connection members 116 on a proximal-facing surface of the plate 112*d* via connectors 118. A second plate 112 is then similarly coupled to the pull members 114 via connection members 116 on a distal-facing side of the second plate 112. The winch system 126 can pull the plates further until both plates 112, 112*d* are within the digester body 110, thereby defining a first compartmentalized chamber 120. The input valve 134 is then aligned with the volume 115 of the chamber 120, which becomes the proximal-most chamber 120*p*.

Manure and/or other organic waste is then fed to the chamber 120*p* over a period of time. In some aspects, the system may be primed to improve the digestion process. After a desired period of time, based for example on utilizing acetogenic and methogenic activity or fill level of the chamber, a second set of pull members is coupled to the proximal facing surface of the second plate 112, a third plate is coupled to the second set of pull members 114, and the winch system 126 pulls the plates 112, 112*d*, and thus the compartmentalized chambers 120, longitudinally in the distal direction. The chambers may remain stationary for a desired period of time, again based for example on utilizing acetogenic and methogenic activity or fill level of the proximal-most chamber. This process is repeated until the entire length of the digester body 110 is occupied by compartmentalized chambers 120 delimited by scraper plates 112, which are coupled by pull members 114.

A series of ports 150 are spaced along the length of the digester body 110 and vent biogas generated via the digestion process within the digester body 110 to a storage vessel 170. It should be understood that the ports 150 are sized and arranged such that they cannot be blocked in the event that plates 112 come rest adjacent the ports 150.

The biogas may pass through a hydrogen sulfide scrubber 160 before reaching the vessel 170. The biogas can then be used to fuel a hot water heater 188 that can be used to heat the digester body 110 or another environment proximate the digestion system 100.

It should be appreciated that each end 111, 113 of the digester body may be sealed with a condom-type member (not shown) made of plastic, rubber, or the like in order to help maintain an anaerobic condition with the digester body 110. The distal end seal may include appropriate openings to allow passage of the pull members 114*d* of the winch system 126 to pass through the seal and to the distalmost plate or plate arrangement. The proximal end seal may include a plate (e.g., steel or polymer) with a peripheral gasket seal.

By providing a mechanically-moving, compartmentalized system, a complete continuous cycle can be developed and 100% uptime efficiency can be reached.

In one exemplary embodiment of the anaerobic digestion system of the disclosure, the inlet of the digester starts with the centerline of the pipe about 3 feet below grade. The digester can have a slight downslope in a proximal-to-distal direction. At this level, an access area formed from concrete blocks and mixed concrete is constructed to allow the placement of steel scraper disks that will compartmentalize the digester into 4-foot to 6-foot chambers. About one-half to one foot in from the start of the digester piping will be the inlet system, which will act as an animal toilet to flush organic waste into the first chamber. A vertical pipe of at least one foot will be placed in this section to connect a spring-loaded butterfly valve to a sloped inlet box recessed to grade of approximately 4-feet.times.2-feet. A grate at grade will cover this inlet box and allow animals to deposit waste directly into the inlet box. The grate covering this box is removable, allowing the sloped inlet box and butterfly valve to be serviceable if needed.

Biogas (60% methane, 40% carbon dioxide) collection will commence after an initial eight feet from the proximal end of the digester body with the installation of vertical pipes (e.g., PVC pipes) having a diameter of about 2 inches spaced four feet apart on center. The two-inch pipe comes up to a T and branches off to a one and one-half inch pipe that will proceed to the heater or gas collection system. The other branch of the T on the two-inch pipe has a removable threaded cap that can be utilized for the sampling of waste and effluent to measure temperature, pH, and microbial population throughout the digester as well as the addition of any needed nutrients or microorganisms. An in-line valve is placed at each of the collection pipes allowing access to the system and control of biogas flow. In order to remove hydrogen sulfide from the biogas, the biogas can be run through a column of iron filings, where the hydrogen sulfide would react with the oxygen and form a solid sulfate. Alternatively, a very small inlet tube (⅛" for a 2" gas take off pipe) can be place so as to introduce oxygen into an anaerobic environment, where the oxygen would oxidize hydrogen sulfide for the production of sulfate, which would fall down into the digestate and provide an additional fertilization source in the end product.

The outlet of the digester body is like the inlet where a retaining wall constructed of concrete block and poured concrete would support the end of the pipe and the earth upon which the pipe lays in. Above the pipe will be a winch or chain fall, which provides a mechanical pulling motion and pulls the scraping disks, made of metal or other rigid material, through the system. This design allows a considerable advantage over other digesters where the length of chain in between each scraper decides the compartment size; this allows for the digester to be scaled up considerably handling larger amounts of waste. Each disk is connected by three distinct chains allowing for an even thrust through the storm water pipe. The winch cable or chain fall will pull a final larger cable or chain from the last scraper and the scraper disk will be removable and transported back to the inlet. The digestate that comes out of the outlet, which is very rich in nitrogen, phosphorus, potassium, and other trace elements, will be used on plant beds, this can be after undergoing a pasteurization process in a heating vessel, which is to be designed.

An additional safety concern may be addressed by designing a French drain system that will allow any effluent that can potentially leak out to be collected and disposed of. Such a French drain system includes laying 2b fill (small rocks) under the digester pipe body, with a perforated drain sloped towards the pipe outlet that protrudes out of the block wall. Under this drain will be a 60 mil thick rubber underlayment liner, which is impermeable to the liquids that will be present in the digester.

The gas collection system will be tied to each of the 8 vertical gas take off ports, which will route the biogas through the potential design for a sulfur scrubber to the gas collection system. This gas collection system includes several expandable bags with individual valves linked in parallel that allow the volume to expand as it fills with gas. This provides both a safety against excessive pressure build up and a means of expanding storage. Additional containers can be attached in series to each other with a connecting pipe and valve.

From the storage devices, the gas will be tapped into and burned in a modified propane water heater; the only change necessary is to change out the nozzle size to increase the flow of biogas to the burner. This water heater will pump hot water both through the high tunnel in the winter and through the ribs of the corrugated storm pipe and will allow the various digester zones to be heated individually with ball valves. This allows for temperature fluctuations between compartments that are utilizing acetogenic bacteria and methogenic bacteria. An additional design includes tapping into the hot water line or adding a boiler device to supplement a pasteurization system for the outflowing digestate to assure the safety of the gardener who is using it.

Figure 6A:
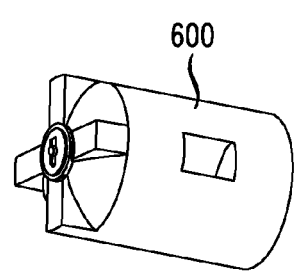
FIG. 6A shows an example digester drum without an attached plate.

FIG. 6A shows an example digester drum 600 without an attached plate. The digester drum 600 in this case has a rectangular hole in the side which may be oriented to collect organic waste. However the size, shape, number and positioning of the hole may vary depending on the various related arrangements. However, the hole can correspond with a pipe, opening, or other conveyance means for depositing the organic matter. While a hole positioned at the top may be useful in many gravity-based organic waste delivery solutions, the hole can be in other positions for other uses. The hole can be arranged to provide a seal with a pipe or tube so that there is no spilling or splashing from the organic waste being deposited into the digester drum 600. The digester drum 600 can be an actual drum or any other size, shape, or material suitable for isolating batches of organic waste from each other, and may not be drum shaped. The term digester drum is used here for consistency with the figures, and can be substituted with container, receptacle, holder, vessel, box, hopper, or similar terminology.

Figure 6B:
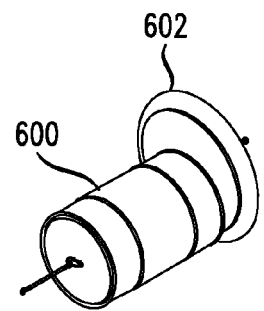
FIG. 6B shows an example digester drum with attached plate.
Figure 6C:
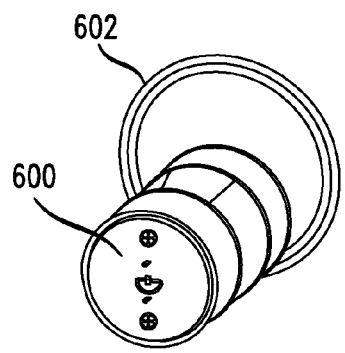
FIG. 6C shows the example digester drum with attached plate of FIG. 6B at a different side angle.
Figure 6D:
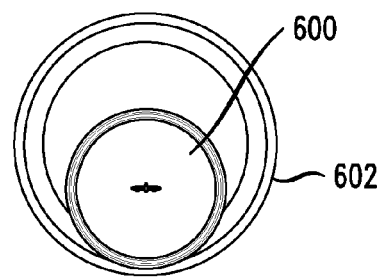
FIG. 6D shows the example digester drum with attached plate of FIG. 6B at a head on angle.
Figure 7:
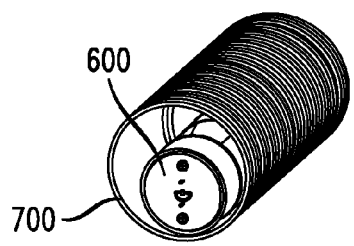
FIG. 7 shows an example digester drum with an attached plate in a tube.
Figure 8:
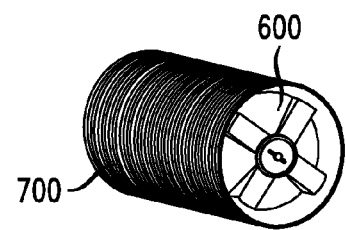
FIG. 8 shows an example digester drum without an attached plate in a tube.

FIG. 6B shows an example digester drum 600 with attached plate 602. FIG. 6C shows the example digester drum 600 with attached plate 602 of FIG. 6B at a different side angle. FIG. 6D shows the example digester drum 600 with attached plate 602 of FIG. 6B at a head on angle. FIG. 7 shows an example digester drum 600 with an attached plate in a tube 700. The plate 602 can be shaped and positioned so as to fit inside the tube 700 when the digester drum 600 is smaller than the interior circumference of the tube 700. FIG. 8 shows an example digester drum 600 without an attached plate in a tube 700. In the case of FIG. 8, no plate is needed because the digester drum 600 is larger and fills or substantially fills the interior space of the tube 700. The digester drum 600 can be replaced with another digester drum when it is full, after a specified amount of time, or when a threshold amount of organic waste has been collected.

The digester drum 600 can be moved in and out of place by pulling, pushing, or otherwise manipulating the digester drum and/or an attached plate, if any. For example, metal clasps, such as carabineers, can be used to attach a pulling mechanism to move the digester drum 600. Other attaching mechanisms can be used that operate according to different principles or that are made of different materials, so long as they are of sufficient strength to move the digester drum 600 and organic waste contained therein.

The digester drum 600 can further ensure that new organic waste never mixes with old organic waste. The organic waste in one digester drum undergoes the process to transform the organic waste and then to further deactivate pathogens. In existing constant feed mixer systems, new organic waste introduces new pathogens into the existing organic waste, causing complications and reducing the predictability of how the microflora and microfauna will react and process the organic waste. As an additional benefit, the digester drum 600 can keep the organic waste confined and less messy. As anaerobic methanogens further degrade the byproduct from acidifying bacteria, heat is generated. Inasmuch as the various microbes involved in the process thrive at different target temperatures, the system disclosed herein can individually regulate the temperature of each digester drum 600 to facilitate a desired microbe performance level.

It will be apparent to those skilled in the art that various modifications and variations can be made to the compartmentalized anaerobic digesters of the present disclosure without departing from the scope of the disclosure. Throughout the disclosure, use of the terms "a," "an," and "the" may include one or more of the elements to which they refer. Other embodiments will be apparent to those skilled in the art from consideration of the specification, as well as from the practice of the principles disclosed herein. It is intended that the specification and examples be considered as exemplary only.

We claim:

1. A method for anaerobic digestion of organic waste, the method comprising:
   receiving organic waste into a first rigid digester drum removably inserted into a digester enclosure configured to accept multiple rigid digester drums therein;
   sliding the first rigid digester drum through the digester enclosure, wherein the first rigid digester drum prevents mixing of the organic waste with other organic waste in a second rigid digester drum that slides through the digester enclosure and that is attached to the first rigid digester drum;
   collecting biogas from the first rigid digester drum and the second rigid digester drum at various ports, each port of the various ports being positioned at a top surface of the digester enclosure and spaced along a length of the digester enclosure; and
   outputting a digestate from the first rigid digester drum and from the second rigid digester drum.

* * * * *